(12) United States Patent
Lei et al.

(10) Patent No.: US 11,167,054 B2
(45) Date of Patent: *Nov. 9, 2021

(54) ACTIVATED DISINFECTANT HYDROGEN PEROXIDE COMPOSITIONS

(71) Applicant: LONZA, LLC, Morristown, NJ (US)

(72) Inventors: Deqing Lei, Alpharetta, GA (US); Philip Gerdon Sweeny, Alpharetta, GA (US)

(73) Assignee: LONZA, LLC, Morristown, NJ (US)

( * ) Notice: Subject to any disclaimer, the term of this patent is extended or adjusted under 35 U.S.C. 154(b) by 35 days.

This patent is subject to a terminal disclaimer.

(21) Appl. No.: 16/850,730

(22) Filed: Apr. 16, 2020

(65) Prior Publication Data

US 2020/0237943 A1    Jul. 30, 2020

Related U.S. Application Data

(63) Continuation of application No. 14/857,403, filed on Sep. 17, 2015, now Pat. No. 10,646,607.

(60) Provisional application No. 62/051,575, filed on Sep. 17, 2014.

(51) Int. Cl.
*A61L 2/18* (2006.01)
*A01N 59/00* (2006.01)

(52) U.S. Cl.
CPC .............. *A61L 2/186* (2013.01); *A01N 59/00* (2013.01)

(58) Field of Classification Search
CPC .......... A61L 2/186; A01N 59/00; A01N 41/04
See application file for complete search history.

(56) References Cited

U.S. PATENT DOCUMENTS

| | | |
|---|---|---|
| 3,915,882 A | 10/1975 | Nirschl et al. |
| 5,264,229 A | 11/1993 | Manning et al. |
| 5,523,012 A | 6/1996 | Winterton et al. |
| 5,558,071 A | 9/1996 | Ward et al. |
| 5,641,530 A | 6/1997 | Chen |
| 6,579,851 B2 | 6/2003 | Goeke et al. |
| 7,354,604 B2 | 4/2008 | Ramirez et al. |
| 7,605,114 B2 | 10/2009 | Rushlow et al. |
| 7,658,953 B2 | 2/2010 | Bobbert |
| 8,461,129 B2 | 6/2013 | Bolduc et al. |
| 8,871,807 B2 | 10/2014 | Gohl et al. |
| 2002/0182103 A1 | 12/2002 | Biering et al. |
| 2005/0192197 A1 | 9/2005 | Man et al. |
| 2006/0035808 A1 | 2/2006 | Ahmed et al. |
| 2006/0052266 A1 | 3/2006 | Johnson |
| 2006/0113506 A1 | 6/2006 | Man et al. |
| 2010/0189599 A1 | 7/2010 | Bobbert |
| 2010/0330196 A1 | 12/2010 | Ramirez et al. |
| 2011/0021812 A1 | 1/2011 | Reinhardt et al. |
| 2011/0028412 A1 | 2/2011 | Cappello et al. |
| 2011/0129435 A1 | 6/2011 | Omidbakhsh |
| 2011/0182958 A1 | 7/2011 | Omidbakhsh |
| 2011/0262557 A1 | 10/2011 | Omidbakhsh |
| 2011/0293741 A1 | 12/2011 | Kawamukai et al. |
| 2012/0164237 A1 | 6/2012 | Ramirez et al. |
| 2012/0177746 A1 | 7/2012 | Ramirez et al. |
| 2012/0225943 A1 | 9/2012 | Gohl et al. |
| 2012/0230869 A1 | 11/2012 | Ramirez et al. |
| 2013/0041004 A1 | 2/2013 | Drager et al. |
| 2013/0071488 A1 | 3/2013 | Suekuni et al. |
| 2013/0084243 A1 | 4/2013 | Goetsch et al. |
| 2013/0096073 A1 | 4/2013 | Sidelman |

FOREIGN PATENT DOCUMENTS

| | | |
|---|---|---|
| CA | 2454437 A1 | 6/2005 |
| EP | 3351772 A2 | 7/1990 |
| EP | 0962520 A1 | 12/1999 |
| EP | 2338343 A1 | 6/2011 |
| EP | 2436265 A2 | 4/2012 |
| WO | 93/14183 A1 | 7/1993 |
| WO | 94/10837 A1 | 5/1994 |
| WO | 99/19432 A1 | 4/1999 |
| WO | 2009124314 A1 | 10/2009 |
| WO | 2010095231 A1 | 8/2010 |
| WO | 2014089633 A1 | 6/2014 |

OTHER PUBLICATIONS

PCT International Search Report and Written Opinion based on corresponding PCT Application No. PCT/JS2015/050717, dated Nov. 16, 2015 (13 pages).
Japanese Patent Office, Office Action issued for corresponding Japanese Application No. 2017-514873, dated Jan. 7, 2020, with English translation (9 pages).
Petrovicova, E. "Hydrogen peroxide in home-care formulations" (https://www.aocs.org/stay-informed/read-inform/featured-articles/hydrogen-peroxide-in-home-care-formulations-november-2011) Nov. 2011, pp. 1-8 (Year: 2011).
Urea (http://www.chemicalland21.com/industrialchem/inorganic/UREA%20HYDROGEN%20PEROXIDE.htm) Jul. 28, 2010, pp. 1-2 (Year: 2010).
"DDAC" Canadian Water Quality Guidelines for the Protection of Aquatic Life. Canadian Council of Ministers of the Environment. 2006, pp. 1-4.
MINTEL GNPD, Instant Fabric Brightener, company: Lion Corporation, MINTEL ID#: 2182077 [online], Sep. 2013, [search date: Dec. 18, 2020], https://www.mintel.com.

(Continued)

*Primary Examiner* — Andrew S Rosenthal
(74) *Attorney, Agent, or Firm* — Dority & Manning, P.A.

(57) ABSTRACT

Activated hydrogen peroxide disinfecting compositions are provided especially for low-foaming applications. A concentrate for dilution by an end-user is provided, which includes a hydrogen peroxide source, a non-surfactant organic sulfonic acid or salt thereof, a non-ionic surfactant, and an optional organic acid. Also provided is a ready-to-use hydrogen peroxide, disinfectant solution including a biocidal amount of hydrogen peroxide, a non-surfactant organic sulfonic acid or salt thereof, a non-ionic surfactant, water as solvent and an optional organic acid. An end-user can disinfect a surface of microorganisms by contacting the surface with the disinfecting composition for an amount of time effective to kill a majority of the microbes located on the surface.

15 Claims, No Drawings

(56) References Cited

OTHER PUBLICATIONS

MINTEL GNPD, Power Laundry Bleach, compamy: Kao, MINTEL ID#: 2531515 [online], Jul. 2014, [search date: Dec. 18, 2020], https://www.mintel.com.
"Trouble in rainy season—Regarding measures against odor of laundry dried indoors"; Kao Information, Kao consumer research center, May 2008, [search date: Dec. 18, 2020 ], https://www.kao.co.jp/content/dam/sites/kao/www-kao-co-jp/lifei/life/pdf/2008 0523,pdf.
Antibacterial and Antifungal Agents, 2006, vol. 34, No. 1, pp. 11-18.
JP Office action for JP2017-514873 dated Feb. 3, 2021, 19 pages.

ACTIVATED DISINFECTANT HYDROGEN PEROXIDE COMPOSITIONS

CROSS-REFERENCE TO RELATED APPLICATION

This application is a continuation of U.S. patent application Ser. No. 14/857,403, filed Sep. 17, 2015, which claims benefit of U.S. provisional application No. 62/051,575, filed Sep. 17, 2014, the disclosure of each of which is incorporated herein by reference.

FIELD OF THE INVENTION

The present invention relates to hydrogen peroxide disinfectants in both concentrate and ready-to-use forms, and more particularly to activated hydrogen peroxide solutions with improved disinfectant and antimicrobial properties.

BACKGROUND OF THE INVENTION

Over the years, efforts have been focused on developing highly active antimicrobial compositions effective against a broad spectrum of microorganisms. However, these compositions also need to have low toxicity against humans and animals and be safe to the environment.

Among the known disinfectants and antimicrobials, hydrogen peroxide is a preferred choice not only due to its potential as a biocide but also due to its low toxicity because it decomposes to give nontoxic oxygen and water. Unfortunately, hydrogen peroxide is not very efficient by itself with its low kill rate against certain organisms although it shows a broad spectrum of biocidal activities and is widely used.

An example of the low kill rate for hydrogen peroxide is that a 6 weight percent ("wt. %") hydrogen peroxide solution, within a 5 minutes contact time, will only exhibit approximately a 3 Log (i.e., 1000-fold) reduction against *Staphylococcus Aureus*, and less than a 2 Log (100-fold) reduction against *Pseudomonas Aeruginosa*. Likewise, a 6000 ppm (i.e., 0.6 wt. %) hydrogen peroxide solution, within a 5 minute contact time, will only exhibit about a 1 log reduction against *Staphylococcus Aureus*, and less than a 1 Log reduction against *Pseudomonas Aeruginosa*.

The killing efficiency of hydrogen peroxide can be improved by using highly concentrated hydrogen peroxide or a longer contact time. However, hydrogen peroxide at a concentration higher than 7.5 wt. % is corrosive. As a result, special handling procedures are required for such concentrations. Additionally, contact times longer than 5 minutes are generally not acceptable for most disinfectant applications.

Because of these difficulties in increasing kill rates, efforts have been made on developing activated hydrogen peroxide formulations to improve the efficacy and killing rate of hydrogen peroxide without having to resort to high hydrogen peroxide concentrations and contact times greater than 5 minutes. The development of these activated hydrogen peroxide formulations is especially important to industries such as the food, health-care, hospitality, and even household use.

One attempt to enhance the efficacy of hydrogen peroxide disinfecting solutions is found in U.S. Pat. No. 5,523,012 to Winterton et al. ("Wintertown"). Wintertown discloses that the addition of anionic sulfosuccinate surfactants to an aqueous, hydrogen peroxide solution improved the killing time against *Aspergillus fumigatus* to 7.1 minutes. However, the improvement in killing time is still far too long for most disinfectant applications.

Another attempt to enhance the efficacy of hydrogen peroxide disinfecting solutions is found in U.S. Pat. No. 5,264,229 to Mannig et al. ("Mannig"). Mannig discloses a process for reducing the overall bacterial count and increasing the shelf life of the aqueous hydrogen peroxide solution by adding sulfo-based surfactants, such as, alkylaryl sulfonates, sulfates, sulfonates of oils and fatty acid, sulfate of alcohols and sulfosuccinates.

In U.S. Pat. No. 7,658,953, a biocidal hydrogen peroxide composition is enhanced by the addition of a surfactant with a structure: R—O—(CH(Y)—CH$_2$—O)$_n$—CH$_2$—COOH, wherein R is C$_6$ to C$_{12}$ alkyl, Y is H or CH$_3$, and n is 3-10. The addition of the surfactant was reported to achieve a Log 6 reduction of bacteria in a bacteria suspension within 1 min upon contact with the composition.

Several other patents and patent publications disclose the addition of anionic surfactants based on sulfonic acid to increase the kill rate of an aqueous hydrogen peroxide disinfecting solution: U.S. Pat. No. 7,354,604, U.S. Publication Nos.: 2010/0330196, 2011/0262557, 2011/0129435, 2011/0182958, 2012/0230869, 2012/0177746, 2012/0164237, and European Publication No.: 2338343. The anionic surfactant is chosen from C$_8$ to C$_{16}$ alkyl aryl sulfonic acids, sulfonated C$_{12}$ to C$_{22}$ carboxylic acids, C$_6$ to C$_{22}$ alkyl diphenyl oxide sulfonic acids, C$_8$ to C$_{22}$ alkyl sulfonic acids, and C$_6$ to C$_{18}$ alkyl or alkenyl esters of sulfosuccinic acids.

However, the use of anionic sulfonic acid-based surfactants is less desired in low foaming applications where disinfection, and not cleaning, is the primary function to be achieved.

In view of these strategies for increasing the kill rate of the aqueous hydrogen peroxide disinfecting solutions, there is still a need for more efficacious biocidal compositions that provide shorter contact times (i.e., faster rates of kill, e.g. 5 minutes or less) without an anionic surfactant. There is also a need aqueous hydrogen peroxide disinfecting solutions with a broader spectrum of activity especially against problematic biocidal targets such as *Staphylococcus aureus*, and *Pseudomonas aeruginosa*.

SUMMARY OF THE INVENTION

It has now been found that the biocidal activity of aqueous hydrogen peroxide solutions can be surprisingly enhanced with the addition of a non-surfactant sulfonic acid or salt thereof, and optionally an additional acid other than the sulfonic acid. One advantage of the present invention is that anionic sulfonic acid-based, surfactants can be avoided. Another advantage is that mineral acids can avoided is so desired. In one embodiment, the present invention provides a hydrogen peroxide, disinfectant concentrate that includes a hydrogen peroxide source, a non-surfactant organic sulfonic acid or salt thereof, a non-ionic surfactant, and an optional acid other than the sulfonic acid described above. In another embodiment, the present invention provides a ready-to-use hydrogen peroxide, disinfectant solution that includes a biocidal amount of hydrogen peroxide, a non-surfactant organic sulfonic acid or salt thereof, a non-ionic surfactant, water as solvent and an optional acid other than the sulfonic acid. In still another embodiment, the present invention provides a method of disinfecting a surface of microorganisms by contacting the surface with the disinfecting composition for an amount of time effective to kill a majority of the microbes located on the surface.

As described above, the present invention in one embodiment provides a hydrogen peroxide, disinfectant concentrate including a hydrogen peroxide source, a non-surfactant organic sulfonic acid or salt thereof, and a non-ionic surfactant. The concentrate is typically a solid formulation in the form of a powder or tablet.

The hydrogen peroxide source provides a hydrogen peroxide concentration typically from about 2 to about 8 weight percent of the total concentrate. Examples of the hydrogen peroxide sources include hydrogen peroxide solution, sodium percarbonate, potassium percarbonate, sodium and potassium perborate, hydrogen peroxide urea, hydrated forms thereof, and mixtures thereof.

Examples of non-surfactant organic sulfonic acids or their salts include a $C_1$-$C_7$ alkylsulfonic acid, a sulfonated $C_1$-$C_7$ carboxylic acid, a substituted or unsubstituted aromatic sulfonic acid, mono-alkylphenylsulfonic acid, a di-alkylphenylsulfonic acid, where the substituted aromatic sulfonic acid is substituted with at least one $C_1$-$C_3$ alkyl group, and mixtures thereof. In another embodiment, the alkylsulfonic acid and the sulfonated carboxylic acid will have a $C_1$-$C_5$ alkyl group. An example of the $C_1$-$C_7$ alkylsulfonic acid includes methanesulfonic acid. An example of the unsubstituted aromatic sulfonic acid includes benzene sulfonic acid. Examples of substituted aromatic sulfonic acids include toluene sulfonic acid, xylenesulfonic acid, ethylbenzene sulfonic acid and mixtures thereof. Examples of salt forms include alkali metal salts, alkaline earth metal salts and ammonium salts. The non-surfactant organic sulfonic acid is typically about 2 to about 15 weight percent of the total concentrate.

In another embodiment of the hydrogen peroxide, disinfectant concentrate, the concentrate can further include an optional acid other than the non-surfactant organic sulfonic acid. The optional acid can be phosphoric acid, etidronic acid, and mixtures thereof. The optional acid can also be a carboxylic acid such as a $C_1$ to $C_8$ mono-, di-, or tricarboxylic acid, a $C_1$ to $C_8$ hydroxyl carboxylic acid, a substituted or unsubstituted aromatic carboxylic acid, and mixtures thereof. In yet another embodiment, the optional acid can be a mineral acid. The optional acid is typically about 0.2 to about 10 weight percent of the total concentrate.

Examples of the nonionic surfactant include a $C_8$ to $C_{14}$ alkylated polyethylene glycol, $C_8$ to $C_{14}$ alkylated polypropylene glycol, polyoxyethylene glycol alkylphenol ethers and glucoside alkyl ethers, or mixtures thereof. The nonionic surfactant is typically about 0.5 to about 8 weight percent of the total concentrate.

In yet another embodiment of the concentrate, the concentrate can further include a hydrogen peroxide stabilizer and a metal corrosion inhibitor. Both the hydrogen peroxide stabilizer and a metal corrosion inhibitor are typically about 0.05 to about 0.5 weight percent of the total concentrate. The concentrate can further include a biocidal quaternary ammonium salt in an amount from about 0.1 to about 10 weight percent of the total concentrate. In another embodiment, the concentrate can further include a zwitterionic surfactant, an ionic surfactant or both. The zwitterionic surfactant and the ionic surfactant, if present, are typically about 0.5 to about 5 weight percent of the concentrate.

As further described above, the present invention in another embodiment provides a ready-to-use hydrogen peroxide, disinfectant solution including a biocidal amount of hydrogen peroxide, a non-surfactant organic sulfonic acid or salt thereof, a non-ionic surfactant, and water. It will be apparent to one skilled in the art that the same above-described components for the concentrate can be the same components for the hydrogen peroxide, the non-surfactant organic sulfonic acid or salt thereof, and the non-ionic surfactant of the ready-to-use solution. For example, just like the concentrate, the non-surfactant organic sulfonic acid of the ready-to-use solution includes a $C_1$-$C_7$ or $C_1$-$C_5$ alkylsulfonic acid, a sulfonated $C_1$-$C_7$ or $C_1$-$C_5$ carboxylic acid, a substituted or unsubstituted aromatic sulfonic acid, mono-alkylphenylsulfonic acid, a di-alkylphenylsulfonic acid, where the substituted aromatic sulfonic acid is substituted with at least one $C_1$-$C_3$ alkyl group and mixtures thereof. An example of the $C_1$-$C_7$ or $C_1$-$C_5$ alkylsulfonic acid includes methanesulfonic acid. An example of the unsubstituted aromatic sulfonic acid includes benzene sulfonic acid. Examples of the substituted aromatic sulfonic acid include toluene sulfonic acid, xylenesulfonic acid, ethylbenzene sulfonic acid and mixtures thereof. Examples of salts include alkali metal salts, alkaline earth metal salts and ammonium salts.

The biocidal amount of hydrogen peroxide in the ready-to-use solution is typically from about 0.05 to about 5.0 weight percent of the total solution. The non-surfactant organic sulfonic acid in the ready-to-use solution is typically about 0.05 to about 5.0 weight percent of the total solution. The nonionic surfactant is in the ready-to-use solution is typically about 0.05 to about 3.0 weight percent of the total solution.

In another embodiment, the ready-to-use solution can further include an optional acid such as a carboxylic acid or a mineral acid (i.e., an inorganic acid). The amount of the carboxylic acid or a mineral acid is typically from about 0.05 to about 6.0 weight percent of the total solution. The solution can have a pH of from about 1.0 to about 4.0. The ready-to-use solution can further include a biocidal quaternary ammonium salt in an amount from about 0.1 to about 5 weight percent of the solution. In another embodiment, the ready-to-use solution can further include a zwitterionic surfactant, an ionic surfactant or both. The zwitterionic surfactant and the ionic surfactant, if present, are typically about 0.5 to about 5 weight percent of the concentrate.

In addition to water, the ready-to-use solution can further include a water-miscible organic solvent. Examples of water-miscible solvents include ethanol, propanol, benzyl alcohol, phenoxyethanol, isopropanol, diethylene glycol propyl ether, ethylene glycol monomethyl ether, ethylene glycol monoethyl ether, ethylene glycol monopropyl ether, ethylene glycol monoisopropyl ether, ethylene glycol monobutyl ether, diethylene glycol monomethyl ether, diethylene glycol monobutyl ether, diethylene glycol monoethyl ether, diethylene glycol mono-n-butyl ether, ethylene glycol dimethyl ether, ethylene glycol diethyl ether, ethylene glycol dibutyl ether, propylene glycol n-butyl ether, tripropylene glycol methyl ether, dipropylene glycol methyl ether, dipropylene glycol butyl ether and combinations thereof.

In yet another embodiment, the present invention provides a method of disinfecting a surface of microorganisms with the ready-to-use solution of the invention. The method includes the step of contacting the surface with a disinfecting composition including (i) a biocidal amount of hydrogen peroxide, (ii) a non-surfactant organic sulfonic acid or salt thereof, (iii) a non-ionic surfactant, and (iv) water, where the surface is contacted for an amount of time effective to kill a majority of the microbes located on the surface. Examples of microorganisms to be killed include Gram positive bacteria, Gram negative bacteria, viruses, fungi, mildew, mold and combinations thereof. More specific examples of microorganisms to be killed include *Staphylococcus, Pseudomonas,* hepatitis, rotavirus, rhinovirus, tuberculosis and combinations thereof. Examples of surfaces to be disinfected with the ready-to-use solution include floors, walls, countertops, appliances, and fixtures.

In one more embodiment, the present invention provides a two-part disinfectant. The two-part disinfectant has a first container including a non-surfactant organic sulfonic acid or salt thereof, and a non-ionic surfactant, and a second container including a biocidal amount of hydrogen peroxide, and water. In a further embodiment, the additional components are included only in the first container.

These and other unique aspects of the present invention will become more readily apparent from the detailed description set forth below.

DETAILED DESCRIPTION OF THE INVENTION

The present invention advantageously provides a hydrogen peroxide disinfectant concentrate, and a ready-to-use hydrogen peroxide disinfectant solution. Further, the present invention provides a method of using the solution to disinfect substrates from troublesome microorganisms such as *Staphylococcus aureus,* and *Pseudomonas aeruginosa.* One unique aspect of the present invention, as compared to the prior art, is that inventive compositions and methods avoid the use of sulfonate-based anionic surfactants typically found in activated hydrogen peroxide formulations. The omission of anionic sulfonic acid-based, surfactants allows the solutions to be used in applications were low foaming is desired or is advantageous.

In accordance with the invention, both the concentrate and the ready-to-use solution include (i) a hydrogen peroxide source, (ii) a non-surfactant organic sulfonic acid or salt thereof, (iii) a non-ionic surfactant, and (iv) an optional additional acid other than the organic sulfonic acid. The ready-to-use solution also includes an aqueous solvent such as water and/or water-miscible organic solvents. Water-miscible organic solvents to be used include: alcoholic solvents such as ethanol, propanol, benzyl alcohol, phenoxyethanol, and isopropanol; and alkyl and dialkyl glycol ethers of ethylene glycol or propylene glycol, such as diethylene glycol propyl ether, ethylene glycol monomethyl ether, ethylene glycol monoethyl ether, ethylene glycol monopropyl ether, ethylene glycol monoisopropyl ether, ethylene glycol monobutyl ether, diethylene glycol monomethyl ether, diethylene glycol monobutyl ether, diethylene glycol monoethyl ether, diethylene glycol mono-n-butyl ether, ethylene glycol dimethyl ether, ethylene glycol diethyl ether, ethylene glycol dibutyl ether, propylene glycol n-butyl ether, tripropylene glycol methyl ether, dipropylene glycol methyl ether, and dipropylene glycol butyl ether. When the water-miscible organic solvent is used with water, it can be diluted in a range with water from about 0.5% to about 20% by weight of water present in the ready-to-use solution. In another embodiment, water-miscible organic solvent is diluted from about 1% to about 5% by weight of water present in the ready-to-use solution.

Hydrogen peroxide sources to be used in the invention include, but are not limited to, aqueous hydrogen peroxide solution, sodium percarbonate, potassium percarbonate, sodium and potassium perborate, hydrogen peroxide urea, as well as their hydrated forms, and mixtures thereof. In one embodiment, the hydrogen peroxide source is an aqueous solution containing about 20 to about 50% by weight hydrogen peroxide dissolved in water. In another embodiment, the hydrogen peroxide source is a solid formulation of sodium percarbonate.

As will be apparent to those skilled in the art, the amount of hydrogen peroxide is variable depending on whether the composition is a concentrate or a ready-to-use solution. The amount of the hydrogen peroxide in the concentrate is from about 1.0 to about 8.0 weight percent ("w/w %") of the total formulation depending on storage stability. As noted above, concentrations above 7.5 w/w % are generally considered corrosive and unstable to many applications. Typically, the concentrate contains from 2 to 7 w/w % of the hydrogen peroxide source. In contrast, the amount of hydrogen peroxide in the ready-to-use solution is a biocidal amount that can range from about 0.05 to about 5.0 w/w % of the total solution depending on application. In another embodiment, the biocidal amount ranges from about 0.05 to about 2.0 w/w %. Typically, the ready-to-use solution contains from 0.1 to 1.5 w/w % of the hydrogen peroxide.

Non-surfactant organic sulfonic acids to be used in the invention include, but are not limited to, a $C_1$-$C_7$ alkylsulfonic acid, a sulfonated $C_1$-$C_7$ carboxylic acid, a substituted or unsubstituted aromatic sulfonic acid, mixtures thereof and salts thereof. In another embodiment, the alkylsulfonic acid and sulfonated carboxylic acid have a $C_1$-$C_5$ chain. In the case of a substituted aromatic sulfonic acid, the aromatic ring is substituted with at least one $C_1$-$C_3$ alkyl group. Stated otherwise, if the aromatic ring is substituted the alkyl group should contain three (3) carbons or less. Salts of the non-surfactant organic sulfonic acid are alkali metal and alkaline earth metals salts, such as sodium, potassium, calcium and magnesium. Salts may also include ammonium salts. Representative examples of the non-surfactant organic sulfonic acid are methane sulfonic acid, benzene sulfonic acid, toluene sulfonic acid, xylenesulfonic acid, ethylbenzene sulfonic acid, and mixtures thereof. The amount of the non-surfactant organic sulfonic acid in concentrate is from about 1 to about 20 w/w % of the total formulation. Typically, the concentrate contains from 3 to 15 w/w % of the non-surfactant organic sulfonic acid. The amount of the non-surfactant organic sulfonic acid in the ready-to-use solution is from about 0.05 (e.g., 0.1) to about 5 w/w % of the total solution. Typically, the ready-to-use solution contains from about 0.5 to about 3 w/w % of the non-surfactant organic sulfonic acid.

The non-ionic surfactants to be used in the invention include, but are not limited to, polyoxyethylene glycol alkyl ethers, octaethylene glycol monododecyl ether, pentaethylene glycol monododecyl ether, polyoxypropylene glycol alkyl ethers, glucoside alkyl ethers, decyl glucoside, lauryl glucoside, octyl glucoside, polyoxyethylene glycol octylphenol ethers, polyoxyethylene glycol alkylphenol ethers, glycerol alkyl esters, polyglycerol esters, glyceryl laurate, polyoxyethylene glycol sorbitan alkyl esters, sorbitan alkyl esters, dodecyldimethylamine oxide, block copolymers of polyethylene glycol and polypropylene glycol, poloxamers and polyethoxylated tallow amine (POEA), and mixtures thereof. The amount of the nonionic surfactant in the concentrate is from about 1 to about 8% w/w % of the formulation. Typically, the concentrate contains from 2 to 5 w/w % of nonionic surfactant. The amount of the nonionic surfactant in the ready-to-use solution is from about 0.05 to about 3 w/w % of the solution. In another embodiment, the nonionic surfactant in the ready-to-use solution is from about 0.05 to about 1.5 w/w % of the solution. Typically, the ready-to-use solution contains from 0.06 to 1 w/w % of the nonionic surfactant.

In accordance to the present invention, there may be an optional acid added to the composition other than the non-surfactant organic sulfonic acid, and in addition to the non-surfactant organic sulfonic acid. The optional acid may be a carboxylic acid or a mineral acid (i.e., an inorganic acid). The optional acid may be added up to an amount of about 10 w/w %.

The optional carboxylic acid which may be used in the present invention, excludes the non-surfactant organic sulfonic acids described herein and includes, but are not limited to, a $C_1$ to $C_8$ mono, di- or tricarboxylic acid, a $C_1$ to $C_8$ hydroxyl carboxylic acid, a substituted or unsubstituted aromatic carboxylic acid. In the case of a substituted aromatic carboxylic acid, the aromatic ring is substituted with at least one alkyl group having three (3) or less carbons. Representative examples of carboxylic acids to be used include, but are not limited to, acetic acid, propionic acid, butyric acid, pentanoic acid, hexanoic acid, octanoic acid, succinic acid, citric acid, oxalic acid, tartaric acid, glutaric acid, adipic acid, benzoic acid, phthalic acid, and mixtures thereof. In one embodiment, the carboxylic acid is acetic acid, octanoic acid, hexanoic acid, succinic acid, citric acid, glutaric acid, adipic acid, and mixtures thereof. The amount of carboxylic acid in the concentrate is from about 0.5 to about 8 w/w % of the formulation. Typically, the concentrate contains from 1 to 5 w/w % of the carboxylic acid, which is dependent on storage stability. The amount of carboxylic acid in the ready-to-use solution is from about 0.01 to about 8.0 w/w % of the solution. Typically, the ready-to-use solution contains from 0.1 to 5.0 w/w % of the carboxylic acid, which is dependent on the storage stability as well as the application of the solution.

Examples of mineral acids include, but are not limited to, phosphoric acid, sulfuric acid and hydrochloric acid. The amount of mineral acid in the concentrate is from about 0.1 to about 10 w/w % of the formulation. Preferably, the concentrate contains from 0.2 to 5 w/w % of the mineral or non-carboxylic, organic acid. The amount of mineral acid in the ready-to-use solution is from about 0.01 to about 0.5% of the solution. Preferably, the ready-to-use solution contains from 0.01 to 0.3 w/w % of the mineral acid.

To alter the pH values, buffers or other pH adjusting agents may be added to the formulations. The amounts of the acids described above may be increased to decrease the pH. To increase the pH, salts of the acids described herein may be used or, basic compounds or solutions, such as sodium hydroxide and potassium hydroxide or the alkali metal and ammonium salts of phosphoric acid, citric acid, and sulfuric acid. The pH of the concentrate is from about 0.5 to about 5, and more preferably from 1 to 3. The pH of the ready-to-use solution is from about 1.0 to about 4.5, and more preferably from 2 to 3.

The concentrate and ready-to-use solution may also contain a biocidal quaternary ammonium salt to increase the biocidal activity of the formulation. Examples of quaternary ammonium salts to be used include, but are not limited to, didecyl dimethyl ammonium chloride ("DDAC") and alkyl dimethyl benzyl ammonium chlorides. The quaternary ammonium salt may be present in the concentrate in an amount from about 0.1 to about 10 weight percent, and in the ready-to-use solution in an amount from about 0.01 to about 2.0 weight percent.

In another embodiment, the concentrate and ready-to-use solution of the may further include a stabilizer to deactivate impurities that can cause hydrogen peroxide decomposition. The stabilizer may be added to prevent the components from decomposing on the shelf prematurely during storage of the formulations. Known stabilizers for use in stabilizing acidic hydrogen peroxide solutions include organic and inorganic sequestering agents, i.e., stannates and phosphates, and combinations of organic compounds, organometallic salts and metal chelators with or without stannates and phosphates. In one embodiment, the stabilizer may be phosphoric acid, if not already present in the composition, a derivative of phosphoric acid, 1-hydroxyethylidenediphosphonic acid (HEDP), phytic acid, aminophosphate, phosphonate and sodium glutamate, $NaH_2PO_4$, $Na_5P_3O_{10}$, organophosphonic acid, amino-phosphonate, silver dihydrogen citrate, diphosphonic acid, ethylenediaminetetraacetic acid (EDTA), N-(hydroxyethyl)-ethylenediaminetriacetic acid (HEDTA), tri(methylene phosphoric acid), diethylenetriaminepenta(methylene phosphoric acid), 2-hydroxy ethylimino bis(ethylene phosphoric acid), citric acid, dipicolinic acid, ethylenediamine-N,N'-disuccinic acid, methylglycinediacetic acid and their alkaline salts thereof, nitriotriacetic acid (NTA), 2-hydroxyethylimino-diacetic acid (HEIDA), and salts thereof, cyclohexane-1,2-diaminotetrakismethylene phosphonic acid or water-sol, diethylenetriamine penta(methylene phosphonic acid), colloidal stannate, diethylenetriamine pentaacetic acid (DTPA), citrate salts, gallate salts, malate salts, malonate salts, oxaloacetate salts, oxalate salts, pyruvate salts, succinate salts, 2-hydroxypyridine-1-oxide (2-HPNO), hydroxyethylidene diphosphonic acid (HEDP) zinc salt, triethanol amine phosphate or mixtures thereof. The hydrogen peroxide stabilizer can be a single component or a mixture of the derivatives of phosphoric acid and the chelators described above. The amount of the optional stabilizer in the concentrate can be from about 0.01% to about 5 w/w %, preferably from 0.05% to 2 w/w %, and more preferably from 0.1% to 1.0 w/w %.

In one another embodiment, the concentrate and ready-to-use solution of the may further include a zwitterionic surfactant, an ionic surfactant, or both. An example of an ionic surfactant includes sodium dodecyl sulfate. The amount of the zwitterionic surfactant and the ionic surfactant can each range in 0.5 to 5 w/w % of the total composition.

Other additives may be also added to the antimicrobial composition of the present disclosure to provide the composition with suitable properties for end use applications. Typical examples include corrosion inhibitors, emulsifiers, fragrances, dyes, preservatives, antifoam agents, thickening agents, hydrotrope agents, and mixtures thereof.

In one embodiment, for instance, the concentrate and ready-to use compositions may include a corrosion inhibitor. Corrosion inhibitors that may be used include, but are not limited to, borates, phosphates, polyphosphates, sodium benzoate, sodium gluconate, sodium silicate, sodium molybdate, sodium bisulfate, benzotriazole or mixtures thereof. When present, the corrosion inhibitor can be contained in the composition in an amount from about 0.001% to about 10% by weight, such as from about 0.01% to about 1% by weight.

In another embodiment, according to present invention, the concentrate formulation is a solid formulation which can be either a powder or in tablet form. In such embodiments, the formulation comprises at least one hydrogen peroxide releasing component chosen from sodium percarbonate, sodium perborate monohydrate, and sodium perborate tetrahydrate, hydrogen peroxide urea adduct, preferably sodium percarbonate, at least one organic acid selected from citric acid, succinic acid and benzoic acid, at least one solid nonionic surfactant, in combination with other ingredients such as stabilizers, corrosion inhibitors, dyes, fragrances and preservatives depending on application.

One advantage of a solid formulation is that some hydrogen peroxide based solutions may be unstable with the hydrogen peroxide concentration diminishing greatly in time due to catalytic decomposition. This may be resolved by a producing a dry powdered formulation with solid ingredients such as toluenesulfonic acid, sodium percarbonate, solid nonionic surfactant and solid organic acid such as citric acid, succinic acid, adipic acid, and other adjuvant materials in the mixture even without the addition of phosphorus-based stabilizers.

The concentrate formulation and the powder form can be dissolved in water by an end-user to produce a ready-to-use solution directly for various applications. For example, disinfectant tablets can be produced in the different size and shapes using the powdered formulation. The end-user can disinfect via a simmer or feeder. The resulting tablets provide practical, convenient and benefits for the end-users, particularly, to disinfect and clean large veterinary and poultry facility and food manufacture, equipment, instrument, and large floor areas. In another embodiment, the concentrate can include all the above described components ingredients but for aqueous hydrogen peroxide and water. The end-user can then add aqueous hydrogen peroxide and water just prior to use.

In accordance with the invention, an end-user can disinfect a surface of harmful microorganisms by contacting the surface with the prepared disinfecting compositions as noted above. The surface is contacted for an amount of time effective to kill a majority of the microbes located on the surface. A "majority" in this context mean a kill rate of at least 50% within one (1) minute of contact. In a more preferred embodiment, the kill rate is a 5 Logic, reduction within one (1) minute of contact. Microorganisms intended to be killed include Gram positive bacteria, Gram negative bacteria, viruses, fungi, mildew, mold or combinations thereof. Specific examples of microorganisms to be killed are Staphylococcus, Pseudomonas, hepatitis, rotavirus, rhinovirus, tuberculosis or combinations thereof.

The hydrogen peroxide may optionally be provided to the end-user separate from the sulfonic acid and nonionic surfactant. That is the composition may be provided as a two-part formulation to the end-user in separate containers and the end-user mixes the two parts together prior to use. In addition, the end-user may also add additional water to the formulation to adjust the formulation to the ready-to-use compositions. Additional components are typically provided to the first part containing the sulfonic acid and nonionic surfactant to prevent possible catalytic decomposition of the hydrogen peroxide during storage.

The disinfectant compositions of the present invention can be used in numerous and diverse applications. In one embodiment, for instance, the compositions of the invention may be used to sanitize or disinfect hard, non-porous surfaces. For example, the composition of the invention is well suited for disinfecting or sanitizing flooring materials, countertops, ceramic surfaces, metal surfaces, glass surfaces, stone surfaces, and the like. The compositions can be used to clean the surfaces, destroy microorganisms on the surface and/or prevent growth of microorganisms on the surface. Likewise, the compositions can be used in the food service industry to disinfect and sanitize food processing equipment and other food processing surfaces or to wash produce, such as vegetables. The compositions can also be used in the healthcare industry to disinfect surfaces, facility, equipment and hospital instruments and equipment, and/or disinfect utensils. The compositions can be used in a concentrated or diluted form depending upon the application.

The following non-limiting examples illustrate the advantageous use of the hydrogen peroxide compositions of the present invention that may be used in wipe in any suitable application where disinfecting, sanitizing, and cleaning and/or bleaching are desired.

EXAMPLES

Example 1

Several formulations were screened for antimicrobial activity against using *Staphylococcus aureus* ("Sa") and *Pseudomonas aeruginosa* ("Pa") using a microtiter plate method. Challenge solutions were prepared for each of the concentrations to be evaluated. The test formulation at twice the desired concentrations were prepared in hard water, and added to a microtiter plate. Inoculum was prepared to $1\times10^8$ CFU, and 100 uL was added to each challenge solution in the microtiter plate. *Staphylococcus aureus* ("Sa") ATCC 6538 and *Pseudomonas aeruginosa* ("Pa") ATCC 15442 were tested.

After the appropriate contact time (either 1 min. or 30 sec.), the samples were neutralized by removing 20 uL of the inoculated-challenge solution and adding 180 uL of neutralizer. Serial dilutions of the neutralized, inoculated-challenge solutions were made in growth media to determine log growth. A control was made with inoculated hard water only to determine maximum growth. Plates were incubated at 35° C. for 2 days before reading results. Each solution was tested in triplicate. Log reduction was calculated using the growth of the control as a baseline. The results are shown in Table 1 below.

TABLE 1

| Sample | | $H_2O_2$ in Sample | # $Log_{10}$ Reduction 1 min contact 0.5% $H_2O_2$ | | # $Log_{10}$ Reduction 1 min contact 0.25% $H_2O_2$ | | # $Log_{10}$ Reduction, 1 min contact 0.1% $H_2O_2$ | | # $Log_{10}$ Reduction 1 min contact 3% PA | |
|---|---|---|---|---|---|---|---|---|---|---|
| ID | Composition | (%) | Pa | Sa | Pa | Sa | Pa | Sa | Pa | Sa |
| 1-1* | $H_2O_2$ | 0.5 | 0 | 0 | | | | | | |
| 1-2* | 3.0% PA | 0.0 | | | | | | | 1.14 | 0.35 |
| 1-3* | 3.0% PA + 5% $H_2O_2$ | 5.0 | 5.7 | 0.28 | | | | | | |

TABLE 1-continued

| Sample ID | Composition | $H_2O_2$ in Sample (%) | # $Log_{10}$ Reduction 1 min contact 0.5% $H_2O_2$ Pa | # $Log_{10}$ Reduction 1 min contact 0.5% $H_2O_2$ Sa | # $Log_{10}$ Reduction 1 min contact 0.25% $H_2O_2$ Pa | # $Log_{10}$ Reduction 1 min contact 0.25% $H_2O_2$ Sa | # $Log_{10}$ Reduction, 1 min contact 0.1% $H_2O_2$ Pa | # $Log_{10}$ Reduction, 1 min contact 0.1% $H_2O_2$ Sa | # $Log_{10}$ Reduction 1 min contact 3% PA Pa | # $Log_{10}$ Reduction 1 min contact 3% PA Sa |
|---|---|---|---|---|---|---|---|---|---|---|
| 1-4* | 5.1% PA + 5.0% Stepanate ® DA-6 + 0.2% HEDP + 5.0% $H_2O_2$ | 5.0 | | | 6.39 | 2.93 | 6.64 | 0.36 | | |
| 1-5 | 4.0% TSA + 3.0% Stepantex ® DA-6 + 0.4% HEDP + 0.4% PA + 5.2% $H_2O_2$ | 5.2 | 4.95 | 4.44 | 6.36 | 6.08 | 1.73 | 0.26 | | |
| 1-6 | 7.0% TSA + 3.0% Stepanate ® DA-6 + 0.8% PA + 5.0% $H_2O_2$ | 5.0 | | | 5.37 | 5.35 | 6.30 | 0.84 | | |
| 1-7 | 7.0% TSA + 3.0% Stepanate ® DA-6 + 3.0% PA + 5.0% $H_2O_2$ | 5.0 | | | 6.39 | 6.16 | 6.64 | 0.71 | | |

*comparative sample;
TSA—toluenesulfonic acid;
PA—phosphoric acid - hydrogen peroxide stabilizer;
HEDP—1-hydroxyethane 1,1-diphosphonic acid - hydrogen peroxide stabilizer; and
Stepanate ® DA-6—a decyl alcohol ethoxylated POE-6 - non-ionic surfactant.

As shown in Table 1, comparative sample 1-1 containing hydrogen peroxide alone showed no antimicrobial efficacy against Pa and Sa. Comparative sample 1-2 containing phosphoric acid alone showed poor antimicrobial efficacy against Pa and Sa. Comparative sample 1-3, a combination of phosphoric acid and hydrogen peroxide, did provide a good activity against Pa (with a 5.7 Logic, reduction) but not against Sa (with a 0.28 Logic, Reduction) at a diluted concentration of 0.5% peroxide. However, comparative sample 1-3 at peroxide concentration of 0.25% and 0.1% was not effective against either Pa or Sa. Comparative sample 1-4, a combination of a nonionic surfactant, Stepanatex® DA-6 and the mixture of hydrogen peroxide and phosphoric acid, also showed improved efficacy against both Pa and Sa. At 0.25% peroxide, sample 1-4 exhibited a 6.39 $Log_{10}$ reduction against Pa. At 0.1% peroxide, sample 1-4 exhibited a 6.64 $Log_{10}$ reduction against Pa. TSA and Stepanatex® DA-6, alone or in combination, were not tested since the compounds are well known not to have antimicrobial activity. Also shown in Table 1 is that the addition of TSA to the combination of peroxide, PA and Stepanatex® DA-6 further enhanced the efficacy of the solution against both Pa and Sa. The data show that the addition of TSA significantly improved the kill rate against Sa.

Example 2

Based on the screening results in example 1, additional formulations containing either toluene sulfonic acid ("TSA") or methane sulfonic acid ("MSA") were evaluated for biocidal activity of using the OECD quantitative method for evaluating bacterial activity on hard non-porous surfaces. See 30 Oct. 2012 Draft—OECD Quantitative Methods for Evaluating the Activity of Microbicides Used on Hard Non-Porous Surfaces. The following raw materials were obtained from Aldrich-Sigma: 50% by weight hydrogen peroxide; 99% by weight citric acid ("CA"); 85% by weight phosphoric acid; 99% by weight glutaric acid ("GA"); 60% by weight 1-hydroxyethane 1,1-diphosphonic acid ("HEDP"); 98% by weight toluenesulfonic acid monohydrate ("TSA"); 95% by weight sodium stannate trihydrate; 99% by weight dipicolinic acid ("DPA"); and 35% by weight S,S-ethylenediamine-N,N'-disuccinic acid trisodium salt ("EDDS"). Stepantex® DA-6, a decyl alcohol ethoxylated POE-6, was obtained from Stepan Company.

Test samples were prepared and evaluated, in which the results are shown in Table 2. Not listed in Table 2 are test samples containing hydrogen peroxide alone that were evaluated at concentrations of 1% by weight.

As in example 1, the efficacy of the hydrogen peroxide solutions were evaluated against *Staphylococcus aureus* ("Sa") ATCC 6538 and *Pseudomonas aeruginosa* ("Pa") ATCC 15442. The test samples were diluted in OECD hard water prepared according to the test methodology to achieve approximately 375 ppm sample+5%/−10% (338-394 ppm) to ascertain the calculated level of hydrogen peroxide based on the amount of hydrogen peroxide used to prepare the formulations. A pass criterion was considered a microbial reduction being a $Log_{10} \geq 4$.

TABLE 2

| Sample ID | Composition | # Log Reduc., 1 min contact 1.0% $H_2O_2$ | | # Log Reduc., 3 min contact 0.5% $H_2O_2$ | |
|---|---|---|---|---|---|
| | | Pa | Sa | Pa | Sa |
| 2-1 | 5% $H_2O_2$ + 8% TSA + 4% Stepantex ® DA-6 + 0.2% HEDP + 3.5% PA (pH: 1.6) | >5.0 | <4.0 | 5.6 | 5.0 |
| 2-2 | 5% $H_2O_2$ + 7% TSA + 3% Stepantex ® DA-6 + 3% GA + 3% PA + 0.2% HEDP (pH: 1.6) | | | 6.0 | 6.1 |
| 2-3 | 5% $H_2O_2$ + 10% TSA + 2% Stepantex ® DA-6 + 2% PA (pH: 1.2) | | | 6.4 | 6.1 |
| 2-4 | 5.0% $H_2O_2$ + 8% MSA + 3% Stepanatex ® DA-6 + 0.1% EDDS (pH ~1.25) | >5.0 | <4.0 | 6.0 | 4.4 |
| 2-5 | 5.0% $H_2O_2$ + 1.5% CA + 8% MSA + 3% Stepanatex ® DA-6 + 0.20% HEDP sodium salt (pH: 1.75) | >5.0 | <4.0 | 5.5 | 4.9 |
| 2-6 | 5.0% $H_2O_2$ + 1.5% CA + 8% TSA + 3% Stepanatex ® DA-6 + 0.20% HEDP sodium salt (pH: 1.78) | >5.0 | <4.0 | 5.5 | 5.7 |
| 2-7 | 5.0% $H_2O_2$ + 1.5% CA + 8% TSA + 1.5% Stepanatex ® DA-6 + 0.20% EDDS (pH: 1.78) | >5.0 | <4.0 | 5.5 | 5.2 |
| 2-8 | 5% $H_2O_2$ + 3% CA + 7% TSA + 3% Stepantex ® DA-6 + 2% PA (pH: 1.3) | | | 6.4 | 5.5 |
| 2-9 | 1.0% $H_2O_2$ + 2% CA + 1.6% TSA + 0.8% Stepanate ® DA-6 + 0.4% PA (pH: 1.68) | 5.28 | <3.9 | | |
| 2-10 | 1.0% $H_2O_2$ + 1.6% TSA + 4.5% CA + 0.4% Stepanatex ® DA-6 + 0.1% EDDS (pH ~1.76) | 6.0 | 6.0 | | |
| 2-11 | 1.0% $H_2O_2$ + 1.6% TSA + 4% CA + 0.4% Stepanate ® DA-6 + 0.1% EDDS (pH ~1.74) | 6.0 | 4.4 | | |

TSA—toluenesulfonic acid;
MSA—methanesulfonic acid;
PA—phosphoric acid;
HEDP—edidronic acid;
GA—glutaric acid;
CA—citric acid;
Stepantex ® DA-6—decyl alcohol ethoxylated POE-6;
EDDS—S,S-ethylenediamine-N,N'-disuccinic acid trisodium salt As shown in Table 2, samples containing MSA exhibited anti-microbial efficacy comparable to samples containing TSA. Samples 2-1 to 2-8 passed with 4 Logic, reductions within 3 minutes against both Pa and Sa. Samples 2-10 and 2-11 additionally containing organic acid, GA and CA, passed with 4 $Log_{10}$ reductions within a much shorter contact time of 1 minute against both Pa and Sa.

Example 3

Samples 2-8 and 2-11 were also tested at their 0.5% $H_2O_2$ level against *Staphylococcus aureus* ATCC 6538 ("Sa") and *Pseudomonas aeruginosa* ATCC 15442 ("Pa") using the AOAC Germicidal Spray Test method in Organic soil load: 5% Fetal Bovine Serum (FBS). The results are shown in Table 3 below. Both samples passed Germicidal Spray test with ≤1/60 Positive/Total Carriers Exposed at 0.5% $H_2O_2$ level within 1 min contact time against both Pa and Sa.

TABLE 3

| Sample# | Contact time | Positive/Total Carriers Exposed | | Log10 Average Dried Carrier Control | |
|---|---|---|---|---|---|
| | | Pa | Sa | Pa | Sa |
| 2-8 | 1 min | 0/60 | 1/60 | 6.69 | 6.42 |
| 2-11 | 1 min | 0/60 | 1/60 | 6.61 | 6.42 |

While the invention has been described above with examples to specific embodiments thereof, it is impossible to cover all scope the invention. Many changes, modification and variations with the process and compositions of the invention will thereof be obvious to those skilled in the art, all of which are within the spirit and scope of this invention without desertion of the inventive concept disclosed herein.

We claim:
1. A ready-to-use hydrogen peroxide, disinfectant solution comprising:
a biocidal amount of hydrogen peroxide from 0.05 to 5 weight percent of the total solution, a non-surfactant organic sulfonic acid or salt thereof from 0.05 to 5.0 weight percent of the total solution,
a non-ionic surfactant from 0.05 to 3.0 weight percent of the total solution,
an optional acid other than the non-surfactant organic sulfonic acid from 0.05 to 6.0 weight percent of the total solution, and
water,
wherein the ready-to-use hydrogen peroxide, disinfectant solution is free of an anionic surfactant,
wherein the ready-to-use hydrogen peroxide, disinfectant solution has a pH from 0.5 to 4.0, and
wherein the hydrogen peroxide source, the non-surfactant organic sulfonic acid or salt thereof, the non-ionic surfactant, and the optional acid provide the ready-to-use hydrogen peroxide, disinfectant solution with a $Log_{10}$ microbial reduction ≥4 within a 3-minute contact time against *Staphylococcus aureus* (Sa),
wherein the non-surfactant organic sulfonic acid or salt thereof is selected from the group consisting of methane sulfonic acid, benzene sulfonic acid, toluene sulfonic acid, xylene sulfonic acid, ethylbenzene sulfonic acid or mixtures thereof, and
wherein the optional acid is glutaric acid, citric acid, phosphoric acid, etidronic acid, or mixtures thereof.

2. The ready-to-use hydrogen peroxide, disinfectant solution of claim 1, wherein the optional acid is glutaric acid or citric acid.

3. The ready-to-use hydrogen peroxide, disinfectant solution of claim 1, wherein the optional acid is etidronic acid.

4. The ready-to-use hydrogen peroxide, disinfectant solution of claim 1, wherein the optional acid is phosphoric acid.

5. The ready-to-use hydrogen peroxide, disinfectant solution of claim 1, wherein the solution has a pH of from 1 to 3.

6. The ready-to-use hydrogen peroxide, disinfectant solution of claim 1, wherein the non-surfactant organic sulfonic acid is methane sulfonic acid.

7. The ready-to-use hydrogen peroxide, disinfectant solution of claim 1, wherein the non-surfactant organic sulfonic acid is benzene sulfonic acid.

8. The ready-to-use hydrogen peroxide, disinfectant solution of claim 1, wherein the non-surfactant organic sulfonic acid is toluene sulfonic acid, xylene sulfonic acid, ethylbenzene sulfonic acid or mixtures thereof.

9. The ready-to-use hydrogen peroxide, disinfectant solution of claim 1, wherein the salt is an alkali metal salt, an alkaline earth metal salt or an ammonium salt.

10. The ready-to-use hydrogen peroxide, disinfectant solution of claim 1, further comprising a biocidal quaternary ammonium salt in an amount from 0.1 to 5 weight percent of the solution.

11. The ready-to-use hydrogen peroxide, disinfectant solution of claim 1, further comprising 0.5 to 5 weight percent of a zwitterionic surfactant.

12. The ready-to-use hydrogen peroxide, disinfectant solution of claim 1, further comprising a water-miscible organic solvent selected from the group consisting of ethanol, propanol, benzyl alcohol, phenoxyethanol, isopropanol, diethylene glycol propyl ether, ethylene glycol monomethyl ether, ethylene glycol monoethyl ether, ethylene glycol monopropyl ether, ethylene glycol monoisopropyl ether, ethylene glycol monobutyl ether, diethylene glycol monomethyl ether, diethylene glycol monobutyl ether, diethylene glycol monoethyl ether, diethylene glycol mono-n-butyl ether, ethylene glycol dimethyl ether, ethylene glycol diethyl ether, ethylene glycol dibutyl ether, propylene glycol n-butyl ether, tripropylene glycol methyl ether, dipropylene glycol methyl ether, dipropylene glycol butyl ether and combinations thereof.

13. The ready-to-use hydrogen peroxide, disinfectant solution of claim 1, further comprising 0.5 to 5 weight percent of an ionic surfactant.

14. The ready-to-use hydrogen peroxide, disinfectant solution of claim 5, wherein the pH is between 1 and 2.

15. The ready-to-use hydrogen peroxide, disinfectant solution of claim 1, wherein the hydrogen peroxide is from 0.05 to 2 weight percent of the total solution.

* * * * *